United States Patent [19]
Zimmerman

[11] Patent Number: 5,888,521
[45] Date of Patent: Mar. 30, 1999

[54] METHOD OF INCREASING CELL RENEWAL RATE

[75] Inventor: Amy C. Zimmerman, Grand Rapids, Mich.

[73] Assignee: Amway Corporation, Mich.

[21] Appl. No.: 902,084

[22] Filed: Jul. 29, 1997

[51] Int. Cl.$^6$ ....................................................... A61K 7/43
[52] U.S. Cl. .......................................... 424/401; 424/70.1
[58] Field of Search ................................ 424/401, 78.02, 424/70.1

[56] References Cited

U.S. PATENT DOCUMENTS

| | | | |
|---|---|---|---|
| 4,014,995 | 3/1977 | Juliano et al. | 424/168 |
| 4,238,509 | 12/1980 | Evans et al. | 424/358 |
| 4,363,815 | 12/1982 | Yu et al. | 424/274 |
| 4,548,728 | 10/1985 | Franklin | 252/174.14 |
| 4,883,659 | 11/1989 | Goodman et al. | 424/78 |
| 5,352,389 | 10/1994 | Gazzani | 252/544 |
| 5,441,740 | 8/1995 | Ozlen | 424/401 |
| 5,449,519 | 9/1995 | Wolf et al. | 424/400 |
| 5,573,785 | 11/1996 | Murphy | 424/70.1 |

FOREIGN PATENT DOCUMENTS

| | | |
|---|---|---|
| 2 597 337 | 10/1987 | France . |
| 2 720 643 | 8/1995 | France . |
| 195 15 609 C1 | 4/1996 | Germany . |

OTHER PUBLICATIONS

Chemical Abstract No. 531391, Embase No. 76115593, *Therapeutic Use of 'AVENA' Skin Cleansing Preparations,* Kuerner H. Karlstr. 29, Karlsruhe Germany West; Z. Hautkr. (Germany, West), 1975, 50/15 (631–635).

Chemical Abstract, No. 12064007, Pascal No. 95–0263947; *Oats: Chemistry, Technology and Potential Uses in the Cosmetic Industry;* Paton, D.; Bresciani, S.; Nam Fong Han; Hart, J.; Journal: Cosmetics and Toiletries; 1995; 110(3) 63–70 (5 p.).

Chemical Abstract, No. 00911864, Pascal No. 76–0006664; *Therapeutischer erfahrungsbericht mit der avena–reihe (Resultats therapeutiques obtenus avec les produits avena);* Kurner H. Ankermann & Co. G.M.B.H., Friesoythe, Journal: Z. Hautkrankh, 1975, 50 (15) 631–635.

Chemical Abstract, No. 001371746; WPI Acc No.: 75–21383W/13; Patent Assignee: Quaker Oats Co.; Priority Data (CC No. Date): US 398651 (730919); US 565695 (750407).

Chemical Abstract, No. 010545082; WPI Acc No. 96–042035/05; Patent Assignee: Clarins; Priority Data (CC No. Date); Fr 946837 (940603).

Chemical Abstract, No. 010338357; WPI Acc. No. 95–240445/31; Patent Assignee: Nurture Inc; Priority Data (CC No Data); US 172485 (931223).

Chemical Abstract, No. 010002632; WPI Acc. No. 94–270343/33; Patent Assignee: (Kono) Konovalov II; Priority Data (CC No Date); SU 5016466 (911228).

Chemical Abstract, No. 009708838; WPI Acc. No. 93/402391/50; Patent Assignee: (Aero=) Aerozol sci prodn assoc; (stal=) stalgen agric firm; Priority Data (CC No Data); Su 4868052 (900921).

Chemical Abstract, No. 00362016; Derwent Accession No.: 73–35329; *A New Natural Ingredient for Cosmetic Formulators;* Assignee: Quaker–Oats (Cleveland Ohio USA); Journal: Drug Cosmet. Ind., 113, No. 3 48, 50, 52, 54, 56, 1973.

Chemical Abstract, No. 124298400; CA: 124 (22)298400u; *Formulating personal care products with hydrolyzed oat protein;* Author(s): Loncar, Clifford; Journal: Household Pers. Prod. Ind.: Date: 1996, vol.: 33; No.: 3; pp. 85–87.

Chemical Abstract, No. 124269972; CA: 124(20)269972(b); *Hair and Scalp Conditioners Containing Oat Extract and Hydroxy Acids;* Inventor (Author) Onitsuka, Satoshi; Dubowoj, Polina; Assignee: Kao Corporation GMBH; Patent: Germany; DE 19515609 C1; Date: 1996 Mar. 28.

Chemical Abstract, No. 123152610; CA: 123(12)152610v; *Oat Oil Compositions with Useful Dermatological Properties ;* Inventor (Author); Potter, Richard; Castro, James M.; Moffatt, Lori C.; Assignee: Nuture, Inc., Patent: PCT International; WO 9517162 A1; Date: 1995 Jun. 29; p. 36 pp.

Chemical Abstract, No. 94109095; CA: 94(14)109095b; *The Water Oat Extracts as Skin Cosmetics;* Assignee: Onodera, Hiroshi; Patent: Japan Kokai Tokkyo Koho JP 80164613; Date: 1980 Dec. 22.

Chemical Abstract, No. 88197417; CA: 88(26)197417n; *Cosmetic Ingredients;* Authors(S): Miller, Aaron; Location: Kalar Lab., Chicago, Ill.; Journal: Soaps, Deterg. Toiletries Rev., Date: 1977; vol.: 7; No.: 9; pp. 21–25.

Chemical Abstract, No. 80030602; CA: 80(6)30602s; *New Natural Ingredient for Cosmetic Formulators;* Author(S): Coe, John; Juliano, Angelo; Journal: Drug Cosmet. Ind.; Date: 1973; vol.: 113; No.: 3; pp.: 48, 50, 52, 54, 56.

Chemical Abstract, No. 0458058; *This Cosmetic Company Really Knows its Oats,* Business Week, Feb. 22, 1993; p. 91; No. 3306.

Chemical Abstract, No. 008399002; WPI Acc No.: 90–286003/38; *Cosmetic Acerola extract–obtd. by washing with water, removing ppte. decolouring and filtering;* Patent Assignee: (Nich–) Nichirei KK; Priority Data (CC No. Date): JP 8916185 (89/01/27).

(List continued on next page.)

Primary Examiner—Thurman K. Page
Assistant Examiner—D. Faulkner
Attorney, Agent, or Firm—Brinks Hofer Gilson & Lione; G. Peter Nichols

[57] ABSTRACT

The present invention relates to a composition for topical use comprising a hydroxycarboxylic acid and oat extract. The present invention also relates to a method of enhancing the rate of skin desquamation by incorporating oat extract into a composition containing hydroxycarboxylic acid. The composition can be topically applied.

20 Claims, No Drawings

OTHER PUBLICATIONS

Chemical Abstract, No. 007353231; WPI Acc No: 87*350237/50; *Two–part skin anti–ageing cosmetic compsn.—contg. active principle hindering skin ageing due to formation and action of free radicals;* Patent Assignee: (Cour) Courtin O; (Clar–) Clarins; Priority Data: (CC No Date ): FR 8416038 (84/10/19).

Chemical Abstract, No. 108226675; CA: (108(26)226675j; *Cosmetic containing antioxidants to delay the aging of skin;* Application: FR 8788 (87/01/07).

*Oats; Chemistry, Technology and Potential Uses in the Cosmetic Industry, High purity oat derivatives show potential as plant–based conditioning ingredients for skin–and hair–care;* David Paton and Sandra Bresciani; Agriculture and Agri–Food Canada, Saskatoon, SK, Canada; Nam Fong Han, Canamino, Inc., Ottawa, ON, Canada; Janice Hart, Canamino Inc., Long Island, NY, USA; Cosmetics & Toiletries Magazine, vol. 110, Mar. 1995, pp. 63–70.

Photocopy of front and back of product container, Vaseline® Brand Intensive Care® Lotion.

METHOD OF INCREASING CELL RENEWAL RATE

BACKGROUND OF THE INVENTION

The present invention relates to a composition to enhance the rate of skin cell renewal or exfoliation and to a method of increasing the skin cell renewal rate. In particular, the present invention relates to a composition containing hydroxycarboxylic acid and an enhancing effective amount of oat extract. The present invention also relates to a method of increasing the rate of skin-cell renewal by applying a composition to the skin, wherein the composition comprises a hydroxycarboxylic acid and an enhancing effective amount of oat extract.

With the aging population, there is a continuing effort to provide cosmetic compositions to improve the appearance of the skin. Thus, many compositions are directed to improving the moisture retaining properties of the skin and consequently, include known moisturizers. At the same time, many consumers seek to use only natural ingredients. As a result, moisturizers such as oatmeal and related oat products have been incorporated into cosmetic compositions.

Recently, in addition to improving the moisture retaining properties of the skin, many compositions have included hydroxycarboxylic acids such as glycolic, lactic, citric, and malic acids in an effort to increase the exfoliation or desquamation of the outermost layer of skin. Thus, cosmetic compositions containing hydroxycarboxylic acids are being marketed for such uses as dry skin, the reduction of wrinkles and fine lines and to combat the effects of aging.

Human skin may be classified into two major parts: the outer layer or epidermis and an underlying layer or dermis. The dermis contains, among other things, blood vessels, nerves, collagen, elastin, and fibroblast cells, which are responsible for the biosynthesis of collagen and elastin.

The epidermis itself also may be considered to consist of two major zones, an inner or malpighian layer and an outer or horny layer. The malpighian layer, a living tissue, may be further divided into basal, spinous, and granular layers. The horny layer, a dead tissue, is also referred to as *stratum corneum*.

In the natural process, basal cells in the basal layer move outward through the spinous and granular layers to become dead cells called corneocytes, in the stratum corneum. The stratum corneum consists of approximately 14 layers of corneocytes. In the normal skin it takes about 14 days for the basal cells to move from the basal layer to the end of the granular layer and to become corneocytes, and another 14 days to reach the outermost layer of the stratum corneum, where they are naturally shed or exfoliated. This process of forming corneocytes is called keratinization, and stratum corneum are the natural products produced by this process. The stratum corneum is the skin tissue that one feels when touching the skin. Usually, it takes about 28 days for cells of the basal layer to move outward to the surface in the course of making new skin.

It is thought that by increasing the natural desquamation rate of the outermost part of the stratum corneum and thus exposing lower layers of the stratum corneum, the appearance of the skin will be improved. Many substances are known to increase the rate of natural desquamation but recently hydroxycarboxylic acids have received an increasing amount of attention. A drawback to the use of hydroxycarboxylic acids is that they can irritate the skin of the user. Thus, it would be desirable to incorporate a substance to reduce the possible irritating effect of the hydroxycarboxylic acid. It would also be desirable to increase the rate of desquamation beyond that provided by the hydroxycarboxylic acid without further increasing the possibility of skin irritation.

SUMMARY OF THE INVENTION

In accordance with the present invention, there is provided a composition for topical use comprising a hydroxycarboxylic acid and oat extract. The oat extract is present in an amount effective to enhance the skin cell desquamation rate of the hydroxycarboxylic acid. It is believed that the oat extract synergistically enhances the rate of skin desquamation when combined with a hydroxycarboxylic acid and, at the same time, reduces the potential for skin irritation from the hydroxycarboxylic acid.

In accordance with this aspect of the present invention, there is provided a composition comprising a hydroxycarboxylic acid and oat extract present in a therapeutically effective amount in topically acceptable vehicle for application to human skin to enhance the rate of skin desquamation provided by the hydroxycarboxylic acid. Surprisingly, the enhancement in the rate of skin desquamation provided by the oat extract does not cause additional skin irritation. To the contrary, the incorporation of the oat extract reduces the potential for skin irritation caused by the hydroxycarboxylic acid.

Generally, the composition contains from about 0.01% to about 99% of a hydroxycarboxylic acid and from about 0.01% to about 99% of oat extract. The oat extract is derived from oat, *avena sativa*. Preferably, the oat extract does not contain β-glucan. In other words, the oat extract does not contain a measurable amount of β-glucan, e.g., less than about 0.01%. The oat extract may be incorporated into a solvent for ease of handling. For example, in a preferred embodiment, the oat extract is incorporated in a 1:1 v/v mixture of 1,3 butylene glycol and water.

Another aspect of the present invention includes a method of increasing the rate of skin exfoliation or desquamation comprising topically applying a composition containing hydroxycarboxylic acid and an enhancing effective amount of oat extract. In this aspect, the method includes topically applying to the skin a composition comprising a hydroxycarboxylic acid and oat extract, in an amount and for a period of time sufficient to increase the rate of natural skin desquamation.

DETAILED DESCRIPTION OF THE INVENTION

In accordance with the present invention, a composition acceptable for topical application to the skin comprises a hydroxycarboxylic acid and oat extract. The hydroxycarboxylic acids can be any of the known hydroxycarboxylic acids but are preferably 2-hydroxycarboxylic acids and related compounds. For convenience, the 2-hydroxycarboxylic acids and related compounds which may be used in accordance with this invention may be classified into three groups, namely (1) 2-hydroxycarboxylic acids, (2) 2-ketocarboxylic acids and esters thereof, and (3) other related compounds. The related compounds may include hydroxycarboxylic acids with the hydroxyl group at any position other than position 2, for example position 3, position 4 or position 5, as well as cyclic hydroxycarboxylic acids (e.g., ascorbic acid and quinic acid), and also may include ketocarboxylic acids and esters thereof. Preferred related compounds include 3-hydroxycarboxylic acids, and 2-ketocarboxylic acids and esters thereof.

GROUP 1

The first group comprises organic carboxylic acids in which one hydroxy group is attached to the 2 position carbon atom of the acid. The generic structure of such 2-hydroxycarboxylic acids may be represented as follows:

($R_a$)($R_b$)C(OH)COOH where $R_a$ and $R_b$ may be the same or different and are independently selected from H, F, Cl, Br, alkyl, aralkyl or aryl group of saturated or unsaturated, isomeric or non-isomeric, straight or branched chain or cyclic form, having 1 to 29 carbon atoms, and in addition $R_a$ and $R_b$ may carry OH, CHO, COOH and alkoxy group having 1 to 9 carbon atoms. 2-Hydroxycarboxylic acids may be present as a free acid or lactone form, or in a salt form with an organic base or an inorganic alkali. 2-Hydroxycarboxylic acids may exist as stereoisomers as D, L, and DL forms when $R_a$ and $R_b$ are not identical.

Typical alkyl, aralkyl and aryl groups for $R_a$ and $R_b$ include methyl, ethyl, propyl, isopropyl, butyl, pentyl, octyl, decyl, dodecyl, hexadecyl, benzyl, and phenyl, etc. 2-Hydroxycarboxylic acids of the first group may be further divided into subgroups comprising (1) alkyl hydroxycarboxylic acids, (2) aralkyl and aryl hydroxycarboxylic acids, (3) polyhydroxy-carboxylic acids, and (4) hydroxy-polycarboxylic acids. The following are representative 2-hydroxycarboxylic acids in each subgroup.

(1) Alkyl Hydroxycarboxylic Acids 1. 2-Hydroxyethanoic acid (Glycolic acid, hydroxyacetic acid)
   (H)(H)C(OH)COOH
2. 2-Hydroxypropanoic acid (Lactic acid)
   ($CH_3$)(H)C(OH)COOH
3. 2-Methyl 2-hydroxypropanoic acid (Methyllactic acid)
   ($CH_3$)($CH_3$)C(OH)COOH
4. 2-Hydroxybutanoic acid
   ($C_2H_5$)(H)C(OH)COOH
5. 2-Hydroxypentanoic acid
   ($C_3H_7$)(H)C(OH)COOH
6. 2-Hydroxyhexanoic acid
   ($C_4H_9$)(H)C(OH)COOH
7. 2-Hydroxyheptanoic acid
   ($C_5H_{11}$)(H)C(OH)COOH
8. 2-Hydroxyoctanoic acid
   ($C_6H_{13}$)(H)C(OH)COOH
9. 2-Hydroxynonanoic acid
   ($C_7H_{15}$)(H)C(OH)COOH
10. 2-Hydroxydecanoic acid
    ($C_8H_{17}$)(H)C(OH)COOH
11. 2-Hydroxyundecanoic acid
    ($C_9H_{19}$)(H)C(OH)COOH
12. 2-Hydroxydodecanoic acid (Alpha hydroxylauric acid)
    ($C_{10}H_{21}$)(H)C(OH)COOH
13. 2-Hydroxytetradecanoic acid (Alpha hydroxymyristic acid)
    ($C_{12}H_{25}$)(H)C(OH)COOH
14. 2-Hydroxyhexadecanoic acid (Alpha hydroxypalmitic acid)
    ($C_{14}H_{29}$)(H)C(OH)COOH
15. 2-Hydroxyoctadecanoic acid (Alpha hydroxystearic acid)
    ($C_{16}H_{33}$)(H)C(OH)COOH
16. 2-Hydroxyeicosanoic acid (Alpha hydroxyarachidonic acid)
    ($C_{18}H_{37}$)(H)C(OH)COOH
17. 2-Hydroxytetraeicosanoic acid (Cerebronic acid)
    ($C_{22}H_{45}$)(H)C(OH)COOH
18. 2-Hydroxytetraeicosenoic acid (Alpha hydroxynervonic acid)
    ($C_{22}H_{43}$)(H)C(OH)COOH

(2) Aralkyl and Aryl 2-Hydroxycarboxylic Acids 1. 2-Phenyl 2-hydroxyethanoic acid (Mandelic acid)
   ($C_6H_5$)(H)C(OH)COOH
2. 2,2-Diphenyl 2-hydroxyethanoic acid (Benzilic acid)
   ($C_6H_5$)($C_6H_5$)C(OH)COOH
3. 3-Phenyl 2-hydroxypropanoic acid (Phenyllactic acid)
   $C_6H_5CH_2$)(H)C(OH)COOH
4. 2-Phenyl 2-methyl 2-hydroxyethanoic acid (Atrolactic acid)
   ($C_6H_5$)($CH_3$)C(OH)COOH
5. 2-(4'-Hydroxyphenyl) 2-hydroxyethanoic acid (4-Hydroxymandelic acid)
   (HO—$C_6H_4$)(H)C(OH)COOH
6. 2-(4'-Chlorophenyl) 2-hydroxyethanoic acid (4-Chloromandelic acid)
   (Cl–$C_6H_4$)(H)C(OH)COOH
7. 2-(3'-Hydroxy4'-methoxyphenyl) 2-hydroxyethanoic acid (3-Hydroxy-4methoxymandelic acid)
   (HO—, $CH_3O$—$C_6H_3$)(H)C(OH)COOH
8. 2-(4'-Hydroxy-3'-methoxyphenyl) 2-hydroxyethanoic acid (4-Hydroxy-3-methoxymandelic acid)
   (HO—, $CH_3O$—$C_6H_3$)(H)C(OH)COOH
9. 3-(2'-Hydroxyphenyl) 2-hydroxypropanoic acid [3-(2'Hydroxyphenyl) lactic acid]
   (HO—$C_6H_4$—$CH_2$)(H)C(OH)COOH
10. 3-(4'-Hydroxyphenyl) 2-hydroxypropanoic acid [3-(4'-Hydroxyphenyl) lactic acid]
    (HO—$C_6H_4CH_2$)(H)C(OH)COOH
11. 2-(3',4'-Dihydroxyphenyl) 2-hydroxyethanoic acid (3,4-Dihydroxymandelic acid)
    (HO—, HO—$C_6H_3$)(H)C(OH)COOH

(3) Polyhydroxy-Carboxylic Acids 1. 2,3-Dihydroxypropanoic acid (Glyceric acid)
   ($HOCH_2$)(H)C(OH)COOH
2. 2,3,4-Trihydroxybutanoic acid (Isomers; erythronic acid, threonic acid)
   ($HOCH_2$ HOCH)(H)C(OH)COOH
3. 2,3,4,5-Tetrahydroxypentanoic acid (Isomers; ribonic acid, arabinoic acid, xylonic acid, lyxonic acid)
   ($HOCH_2$ HOCH HOCH)(H)C(OH)COOH
4. 2,3,4,5,6-Pntahydroxyhexanoic acid (Isomers; allonic acid, altronic acid, gluconic acid, mannoic acid, gulonic acid, idonic acid, galactonic acid, talonic acid)
   ($HOCH_2$ HOCH HOCH HOCH)(H)C(OH)COOH
5. 2,3,4,5,6,7-Hexahydroxyheptanoic acid (Isomers; gluco-heptonic acid, galactoheptonic acid etc.)
   ($HOCH_2$ HOCH HOCH HOCH HOCH)(H)C(OH)COOH

(4) Hydroxy-Polycarboxylic Acids 1. 2-Hydroxypropane-1,3-dioic acid (Tartronic acid)
   (HOOC)(H)C(OH)COOH 2. 2-Hydroxybutane-1,4-dioic acid (Malic acid)
   (HOOC CH$_2$)(H)C(OH)COOH
3. 2,3-Dihydroxybutane-1,4-dioic acid (Tartaric acid)
   (HOOC HOCH)(H)C(OH)COOH
4. 2-Hydroxy-2-carboxypentane-1,5-dioic acid (Citric acid)
   (HOOC CH$_2$)$_2$C(OH)COOH2,3,4,5-Tetrahydroxyhexane-1,6-dioic acid
   (Isomers; saccharic acid, mucic acid etc.)
   HOOC(CHOH)$_4$COOH The 2-hydroxycarboxylic acids may be present in forms other than the acid, such as, for example, salts or lactones. Typical lactone forms which may be used in accordance with this invention include, for example, gluconolactone, galactonolactone, glucuronolactone, galacturonolactone, gulonolactone, ribonolactone, saccharic acid lactone, pantoyllactone, glucoheptonolactone, mannonolactone, and galactoheptonolactone.

GROUP 2

The second group, which comprises compounds related to the 2-hydroxycarboxylic acids, includes organic carboxylic acids in which one keto group is attached to position 2 carbon atom of the acid. The generic structure of such 2-ketoacids may be represented as follows:

(R$_c$)COCOO(R$_d$)

wherein R$_c$ and R$_d$ can be the same or different and are each selected from H, alkyl, aralkyl or aryl group of saturated or unsaturated, isomeric or non-isomeric, straight or branched chain or cyclic form, having 1 to 29 carbon atoms, and in addition R$_c$ may carry F, Cl, Br, I, OH, CHO, COOH and alkoxy group having 1 to 9 carbon atoms. The alpha ketoacids may be present as a free acid or an ester form, or in a salt form with an organic base or an inorganic alkali. The typical alkyl, aralkyl and aryl groups for R$_c$ and R$_d$ include methyl, ethyl, propyl, 2-propyl, butyl, pentyl, hexyl, octyl, dodecyl, hexadecyl, benzyl and phenyl.

In contract to 2-hydroxycarboxylic acids of the first group compounds, the ester form of 2-ketocarboxylic acids has been found to be therapeutically effective for signs and symptoms of cutaneous aging including intrinsic and extrinsic aging. For example, while methyl 2-hydroxypropanoate and ethyl 2-hydroxypropanoate have minimal effects, methyl 2-ketopropanoate and ethyl 2-ketopropanoate are therapeutically very effective. The real mechanism for such difference is not known. We have speculated that the ester form of the 2-ketocarboxylic acid is chemically and/or biochemically very reactive, and a free 2-ketocarboxylic acid may be released in the skin after penetration through the stratum corneum of the skin. The representative 2-ketocarboxylic acids and their esters of the second group are listed below:

1. 2-Ketoethanoic acid (Glyoxylic acid)
   (H)COCOOH
2. Methyl 2-ketoethanoate
   (H)COCOOCH$_3$
3. 2-Ketopropanoic acid (Pyruvic acid)
   CH$_3$COCOOH
4. Methyl 2-ketopropanoate (Methyl pyruvate)
   CH$_3$COCOOCH$_3$
5. Ethyl 2-ketopropanoate (Ethyl pyruvate)
   CH$_3$COCOOC$_2$H$_5$
6. Propyl 2-ketopropanoate (Propyl pyruvate)
   CH$_3$COCOOC$_3$H$_7$
7. 2-Phenyl-2-ketoethanoic acid (Benzoylformic acid)
   C$_6$H$_5$ COCOOH
8. Methyl 2-phenyl-2 ketoethanoate (Methyl benzoylformate)
   C$_6$H$_5$COCOOCH$_3$
9. Ethyl 2-phenyl-2-ketoethanoate (Ethyl benzoylformate)
   C$_6$H$_5$COCOOC$_2$H$_5$
10. 3-Phenyl-2-ketopropanoic acid (Phenylpyruvic acid)
    C$_6$H$_5$CH$_2$ COCOOH
11. Methyl 3-phenyl-2-ketopropanoate (Methyl phenylpyruvate)
    C$_6$H$_5$CH$_2$COCOOCH$_3$
12. Ethyl 3-phenyl-2-ketopropanoate (Ethyl phenylpyruvate)
    C$_6$H$_6$CH$_2$COCOOC$_2$H$_5$
13. 2-ketobutanoic acid
    C$_2$H$_5$COCOOH
14. 2-Ketopentanoic acid
    C$_3$H$_7$COCOOH
15. 2-Ketohexanoic acid
    C$_4$H$_9$COCOOH
16. 2-Ketoheptanoic acid
    C$_5$H$_{11}$COCOOH
17. 2-Ketooctanoic acid
    C$_6$H$_{13}$COCOOH
18. 2-Ketododecanoic acid
    C$_{10}$H$_{21}$COCOOH
19. Methyl 2-ketooctanoate
    C$_6$H$_{14}$COCOOCH$_3$

GROUP 3

The third group, which also comprises related compounds, includes, among others, hydroxycarboxylic acids where the hydroxy is at a position other than position 2, and cyclic hydroxycarboxylic acids which are useful for topical application to improve signs of aging skin and the cutaneous appendages. The members of this group, which are more conveniently identified by name than by generic structures, include salicylic and other beta-hydroxy carboxylic acids as well as, ascorbic acid, quinic acid, isocitric acid, tropic acid (2-phenyl 3-hydroxypropanoic acid), trethocanic acid, 3-chlorolactic acid, citramalic acid, agaricic acid, alcuritic acid, pantoic acid, lactobionic acid and hexulosonic acid.

The oat extract is a plant extract derived from oats, *avena sativa*. The oat extract can be incorporated into a number of solvents for ease of use. In the preferred, embodiment, the oat extract is in a 1:1 v/v mixture of 1,3 butylene glycol and water. Thus, in this mixture, the oat extract is present in an amount of about 10% with the butylene glycol and water being present in an amount of about 45%. In this preferred embodiment, the oat extract is obtained from Canamino Inc. under their trade name Ostar™ Arriveen BG.

Surprisingly, the advantageous results achieved by the incorporation of the oat extract are realized even though the oat extract contains no measurable amount of β-glucan. The term "no measurable amount" as used in the specification and claims means that the oat extract contains less than about 1%, preferably less than about 0.1%, and more preferably less than about 0.01% of β-glucan.

To prepare a therapeutic composition in solution form at least one of the aforementioned hydroxycarboxylic acids and oat extract are incorporated into pharmaceutically acceptable vehicles. Desirably, the hydroxycarboxylic acid is selected from the group consisting of lactic acid, malic acid, citric acid, glycolic acid and mixtures thereof.

The concentration of hydroxycarboxylic acid may range from about 0.01 to about 99 percent by weight of the total composition. Preferably, the concentration of hydroxycarboxylic acids ranges from about 0.1% to about 70%, more preferably from about 1% to about 15%, and desirably from about 1% to about 10%.

The concentration of the oat extract ranges from about 0.01 to about 99 percent by weight of the total composition. Preferably, the concentration of oat extract ranges from about 0.05% to about 30%, more preferably from about 0.1% to about 10%.

Desirably, the ratio of hydroxycarboxylic acid to oat extract ranges from about 1:1 to about 100:1. It is believed that when the ratio of the hydroxycarboxylic acid to the oat extract is within this range that irritation of acid is reduced and cell renewal rate is incremental. Within this ratio, it is desired to have a composition with a pH between about 3.0 and about 5.0, preferably between about 3.5 and about 4.5.

Therapeutic compositions of the present invention may be formulated as a solution, gel, lotion, cream ointment, or other pharmaceutically acceptable form. The compositions of the present invention may also contain various known and conventional cosmetic ingredients so long as they do not detrimentally affect the desired enhancement of skin desquamation. For example, cosmetic ingredients such as alcohols, fats and oils, surfactants, fatty acids, silicones, humectants, moisturizers, viscosity modifiers, emulsifiers, stabilizers, coloring agents, and perfumes or fragrances may be included.

In accordance with one aspect of the present invention, the rate of natural skin desquamation may increased by topical application to the skin of the above composition. In this regard, the present invention encompasses a method of enhancing the rate of natural skin desquamation comprising topically applying to the skin a composition comprising a hydroxycarboxylic acid and oat extract in an amount and for a period of time sufficient to increase the rate of natural skin desquamation. Preferably, the composition is as described above.

Generally, the topical application is on at least a daily basis and may be applied for any suitable period of time. Within a few days, a user may notice improvement in skin texture and smoothness.

The present invention also includes a method of enhancing a composition used for skin desquamation and including a hydroxycarboxylic acid wherein the method includes incorporating an enhancing effective amount of oat extract.

The following are illustrative examples of formulations and compositions according to this invention. Although the examples use only selected compounds and formulations, it should be understood that the following examples are illustrative and not limited. Thus, any of the aforementioned hydroxycarboxylic acids and related compounds may be substituted according to the teachings of this invention in the following examples.

Table 1 sets forth a preferred embodiment of the present invention.

TABLE 1

| INGREDIENT | AMOUNT (wt %) |
|---|---|
| D.I. Water | 70.54 |
| PEG-20 (Polyethylene Glycol) | 5.00 |

TABLE 1-continued

| INGREDIENT | AMOUNT (wt %) |
|---|---|
| Lactic Acid (88%) | 4.50 |
| Glycerin | 4.00 |
| Butylene Glycol | 3.00 |
| Lactic Acid/Citric Acid/Malic Acid/Green Tea Extract | 3.00 |
| Acerola Extract Fermentate | 3.00 |
| Sodium PCA | 2.00 |
| NaOH (50%) | 1.40 |
| Oat Extract (Arriveen BG) | 1.00 |
| Pantenol | 0.50 |
| Thickeners, extracts, preservatives, skin conditioners | 2.06 |

Table 2 presents several examples of formulas falling within the scope of the present invention with the amounts provided being expressed as weight percent.

TABLE 2

| Ingredient | Example 1 | Example 2 | Example 3 | Example 4 | Example 5 | Example 6 |
|---|---|---|---|---|---|---|
| D.I. Water | 70 | 70 | 70 | 70 | 70 | 70 |
| AHA (includes a mixture of one or more of lactic acid, citric acid, malic acid and/or glycolic acid) | 3 | 3 | 5 | 5 | 10 | 10 |
| Oat Extract (Arriveen BG) | 1 | 3 | 1 | 2 | 1 | 5 |
| Skin lotion ingredients including thickeners, extracts, preservatives, skin conditioners | balance | balance | balance | balance | balance | balance |

In order to determine whether compositions containing hydroxycarboxylic acids and oat extract were therapeutically effective in enhancing the natural rate of skin desquamation the following tests were conducted. The skin cell renewal, irritation level and therapeutic index were measured according to the procedure described in *Soap/Cosmetics/Chemical Specialties for September* 1993 at pp.55–59.

TABLE 3

| Formula | Total % AHA* | % Panthenol | % Oat Extract | % Cell Renewal | Irritation Level | Therapeutic Index |
|---|---|---|---|---|---|---|
| A | 3.0 | 2.0 | — | 12.2 | 11.4 | 10.7 |
| B | 3.0 | 2.0 | — | 19.2 | 13.4 | 14.0 |
| C | 3.0 | 2.0 | — | 19.8 | 15.6 | 11.5 |
| D | 3.0 | 0.5 | — | 21.4 | 16.8 | 12.7 |
| E | 5.0 | 2.0 | — | 19.8 | 14.2 | 14.0 |
| F | 5.0 | 0.5 | — | 18.9 | 14.1 | 13.4 |
| G | 5.0 | 0.5 | 1.0 | 30.3 | 12.3 | 23.3 |
| H | 5.0 | 0.5 | 1.0 | 25.6 | 14.5 | 18.0 |
| I | 8.0 | 0.1 | 1.0 | 24.4 | 12.2 | 20.0 |
| J | 5.0 | .05 | 1.0 | 26.6 | 11.2 | 23.8 |
| K | 5.0 | .05 | 1.0 | 28.0 | 12.1 | 23.1 |

AHA refers to the total amount of hydroxycarboxylic acid selected from glycolic acid, malic acid, citric acid, lactic acid and mixtures thereof.

The results show that the addition of the oat extract surprisingly and unexpectedly increased cell renewal rate while maintaining or reducing irritation to levels below that when no oat extract is incorporated.

It should be understood that a wide range of changes and modifications can be made to the compositions and methods of this invention. It is therefore intended that the foregoing description illustrates rather than limits this invention, and that it is the following claims, including all equivalents, which define this invention.

What is claimed:

1. A composition comprising a hydroxycarboxylic acid and oat extract, wherein the oat extract contains less than about 1% β-glucan. the acid and oat extract being present in an amount effective to enhance mammalian skin exfoliation rate.

2. The composition of claim 1 wherein the hydroxycarboxylic acid is represented by a generic structure of:

$R_a R_b C(OH)COOH$ wherein $R_a$ and $R_b$ may be the same or different and are independently selected from H, F, Cl, Br, alkyl, aralkyl or aryl group of saturated or unsaturated, isomeric or non-isomeric, straight or ranched chain or cyclic form, having 1 to 29 carbon atoms, and in addition $R_a$ and $R_b$ can be substituted by OH, CHO, COOH and alkoxy group having 1 to 9 carbon atoms, said hydroxycarboxylic acid may be present as a free acid or lactone form, or in a salt form with an organic base or an inorganic alkali, and as stereoisomers as D, L, and DL forms when $R_a$ and $R_b$ are not identical.

3. The composition of claim 2 wherein the hydroxycarboxylic acid is selected from the group consisting of glycolic, malic, citric, and lactic acid, salts thereof and mixtures thereof.

4. The composition of claim 1 wherein the oat extract contains less than about 0.1% by weight β-glucan.

5. The composition of claim 4 wherein the hydroxycarboxylic acid is selected from the group consisting of glycolic, malic, citric, and lactic acid, salts thereof and mixtures thereof.

6. A method of enhancing the rate of mammalian skin exfoliation comprising topically applying to the skin a composition comprising a hydroxycarboxylic acid and oat extract, wherein the oat extract contains less than about 1% β-glucan.

7. The method of claim 6 wherein the hydroxycarboxylic acid is represented by a generic structure of:

$R_a R_b C(OH)COOH$ wherein $R_a$ and $R_b$ may be the same or different and are independently selected from H, F, Cl, Br, alkyl, aralkyl or aryl group of saturated or unsaturated, isomeric or non-isomeric, straight or ranched chain or cyclic form, having 1 to 29 carbon atoms, and in addition $R_a$ and $R_b$ can be substituted by OH, CHO, COOH and alkoxy group having 1 to 9 carbon atoms, said hydroxycarboxylic acid may be present as a free acid or lactone form, or in a salt form with an organic base or an inorganic alkali, and as stereoisomers as D, L, and DL forms when $R_a$ and $R_b$ are not identical.

8. The method of claim 7 wherein the hydroxycarboxylic acid is selected from the group consisting of glycolic, malic, citric, and lactic acid, salts thereof and mixtures thereof.

9. The method of claim 6 wherein the oat extract contains less than about 0.1% of β-glucan.

10. The method of claim 9 wherein the hydroxycarboxylic acid is selected from the group consisting of glycolic, malic, citric, and lactic acid, salts thereof and mixtures thereof.

11. The method of claim 6, wherein the composition is formulated as a solution, gel, lotion, cream or ointment.

12. The method of claim 6 wherein the composition is topically applied in an amount and for a period of time sufficient to enhance the rate the skin desquamation.

13. The method of claim 12 wherein the topical application is on at least a daily basis.

14. The composition of claim 1 further comprising a topically acceptable vehicle for topical application.

15. The composition of claim 1, wherein the pH is between about 3.5 and 4.5.

16. The composition of claim 1 wherein the oat extract is present in an amount effective to enhance the mammalian skin exfoliation rate of the hydroxycarboxylic acid.

17. A method of increasing the mammalian skin exfoliation rate of a topical composition containing a hydroxycarboxylic acid comprising adding an effective amount of an oat extract, wherein the oat extract contains less than about 1% β-glucan.

18. A composition comprising a hydroxycarboxylic acid, oat extract, and acerola fermentate, wherein the oat extract contains less than about 1% β-glucan, the acid and oat extract being present in an amount effective to enhance mammalian skin exfoliation rate.

19. A method of enhancing the rate of mammalian skin exfoliation comprising topically applying to the skin a composition comprising a hydroxycarboxylic acid, acerola fermentate, and oat extract, wherein the oat extract contains less than about 1% β-glucan.

20. A method of increasing the mammalian skin exfoliation rate of a topical composition containing a hydroxycarboxylic acid comprising adding an effective amount of an oat extract, wherein the oat extract contains less than about 1% β-glucan, and acerola fermentate.

* * * * *

UNITED STATES PATENT AND TRADEMARK OFFICE
CERTIFICATE OF CORRECTION

PATENT NO. : 5,888,521
DATED : March 30, 1999
INVENTOR(S) : Amy C. Zimmerman

Page 1 of 1

It is certified that error appears in the above-identified patent and that said Letters Patent is hereby corrected as shown below:

In the Claims

In claim 1, line 3, please change "β-glucan. the" to --β-glucan, the--.

Signed and Sealed this

Seventeenth Day of April, 2001

Attest:

NICHOLAS P. GODICI

Attesting Officer    Acting Director of the United States Patent and Trademark Office